United States Patent [19]
Lin et al.

[11] Patent Number: 5,885,825
[45] Date of Patent: Mar. 23, 1999

[54] BIOCHEMICAL TRANSFORMATION OF COALS

[75] Inventors: Mow S. Lin, Rocky Point; Eugene T. Premuzic, East Moriches, both of N.Y.

[73] Assignee: Brookhaven Science Associates, Upton, N.Y.

[21] Appl. No.: 344,126

[22] Filed: Nov. 23, 1994

Related U.S. Application Data

[60] Continuation-in-part of Ser. No. 169,417, Dec. 20, 1993, abandoned, which is a division of Ser. No. 905,391, Jun. 29, 1992, Pat. No. 5,297,625, which is a continuation-in-part of Ser. No. 571,917, Aug. 24, 1990, abandoned.

[51] Int. Cl.$^6$ .................................. B09B 3/00; C12N 1/12
[52] U.S. Cl. ...................... 435/262.5; 435/262; 435/245; 435/252.1
[58] Field of Search ................................. 435/262.5, 262, 435/245, 248, 244, 252.1, 822, 170, 171, 281, 282

[56] References Cited

U.S. PATENT DOCUMENTS

| | | | |
|---|---|---|---|
| H1074 | 7/1992 | Lazaroff et al. | 204/105 R |
| 2,413,278 | 12/1946 | Zobell | 435/262 |
| 2,660,550 | 11/1953 | Updegraff et al. | 435/252.1 |
| 4,206,288 | 6/1980 | Detz et al. | 435/267 |
| 4,562,156 | 12/1985 | Isbister et al. | 435/252.1 |
| 4,632,906 | 12/1986 | Kopacz | 435/282 |
| 4,659,670 | 4/1987 | Stevens, Jr. et al. | 435/262 |
| 4,775,627 | 10/1988 | Attia et al. | 435/262 |
| 4,808,535 | 2/1989 | Isbister et al. | 435/252.1 |
| 4,851,350 | 7/1989 | Stevens et al. | 435/262 |
| 4,905,761 | 3/1990 | Bryant | 435/252.4 |
| 4,960,699 | 10/1990 | Wood et al. | 435/166 |
| 5,002,888 | 3/1991 | Kilbane | 435/252.31 |
| 5,036,013 | 7/1991 | Wood et al. | 435/281 |
| 5,092,909 | 3/1992 | Werner et al. | 44/622 |

OTHER PUBLICATIONS

Ruiz–Alares et al., Microbiol. Espan., vol. 34, pp. 11–16, 1981.
Francis et al., Resources Conservation and Recycling, vol. 1, pp. 327–330, 1988.
Jones et al., J. Appl. Bact., vol. 35, pp. 395–404, 1972.
Gokcay et al., Fuel, vol. 62, pp. 1223–1224, 1983.
Helle et al., Dechema Biotechnol. Conf., 6 Meet . . . , 1988, pp. 205–217.
Concise Dictionary of BioMedicine and Molecular Biology, CRC Press 1995, pp. 596–597.
Lin, M.S., et al., "Biodegradation of Coals," *Fuel*, 72 (12) 1667–72, (Dec. 1993).
Francis, A.J., et al., "Influence of Complex Structure on the Biodegradation of Iron–Citrate Complexes," *Applied and Environmental Microbiology*, vol. 59, No. 1, pp. 109–113, (Jan. 1993).
Kearns, J.T., et al., "Application of XPS to the Study of MIC," *Materials Performance*, vol. 31, No. 10, pp. 48–51, (Oct. 1992).
Francis, A.J., et al., "Biodegradation of Metal Citrate Complexes and Implications for Toxic–Metal Mobility," *Nature*, vol. 356, pp. 140–142, (Mar. 1992).
Premuzic, E.T., et al., "Effects of Selected Thermophilic Microorganisms on Crude Oils at Elevated Temperatures and Primers," *BNL 47046*, (Dec. 1991).
Premuzic, et al., "Proceedings: 1991 Second International Symposium on the Biological Processing of Coal," *EPRI GS–7482*, pp. 81–91, (Sep. 19, 1991).
Francis, A.J., et al., "Dissolution of Ferrites by Clostridum sp.," *Geomichrobiology Journal*, vol. 9, pp. 27–40, (May 1991).
Francis, A.J., et al., "Microbial Transformations of Uranium in Wastes," *Radiochimicha Acta*, vol. 52/53, pp. 311–316 (1991).
Francis, A.J. et al., "Anaerobic Microbial Remobilization of Toxic Metals Coprecipitated with Iron Oxide," *Environmental Science Technology*, vol. 24, pp. 373–378, (Mar. 1990).
Francis, A.J., "Microbial Dissolution and Stabilization of Toxic Metals and Radionuclides in Mixed Wastes," *Experientia 46 Birkhäuser Verlag*, vol. 46, pp. 840–851, (1990).
Francis, A.J., et al. "Aerobic and Anaerobic Microbial Dissolution of Toxic Metals from Coal Wastes: Mechanism of Action," *Environmental Science & Technology*, vol. 23, pp. 435–441, (Apr. 1989).
Francis, A.J., et al., "Microbial Dissolution of Toxic Metals from Coal Residues," *Resources, Conservation and Recycling*, 1 P327–330, (1988).
Francis, A.J., et al., "Anaerobic Microbial Dissolution of Transition and Heavy Metal Oxides," *Applied and Environmental Microbiology*, vol. 54, No. 4, pp. 1009–1014, (Apr. 1988).
Berry, D.F., et al., "Microbial Metabolism of Homocyclic and Heterocyclic Aromatic Compounds under Anaerobic Conditions," *Microbiological Reviews*, vol. 51, No. 1, pp. 43–59, (Mar. 1987).
Francis, A.J., et al., "Effects of Lead Oxide and Iron on Glucose Fermentation by Clostridium sp.," *Arch. Environ. Contam. Toxicol.*, vol. 16, pp. 491–497, (1987).
Francis, A.J., et al., "Anaerobic Bacterial Dissolution of Lead Oxide," *Arch. Environ. Contam. Toxicol.*, vol. 15, pp. 611–616, (1986).
Gokcay, C.F., et al., "Microbial Desulphurization of Lignites by a Thermophilic Bacterium," *Fuel*, vol. 62, pp. 1223–1224, (Oct. 1983).

*Primary Examiner*—Irene Marx
*Attorney, Agent, or Firm*—Margaret C. Bogosian

[57] ABSTRACT

A method of biochemically transforming macromolecular compounds found in solid carbonaceous materials, such as coal is provided. The preparation of new microorganisms, metabolically weaned through challenge growth processes to biochemically transform solid carbonaceous materials at extreme temperatures, pressures, pH, salt and toxic metal concentrations is also disclosed.

13 Claims, 4 Drawing Sheets

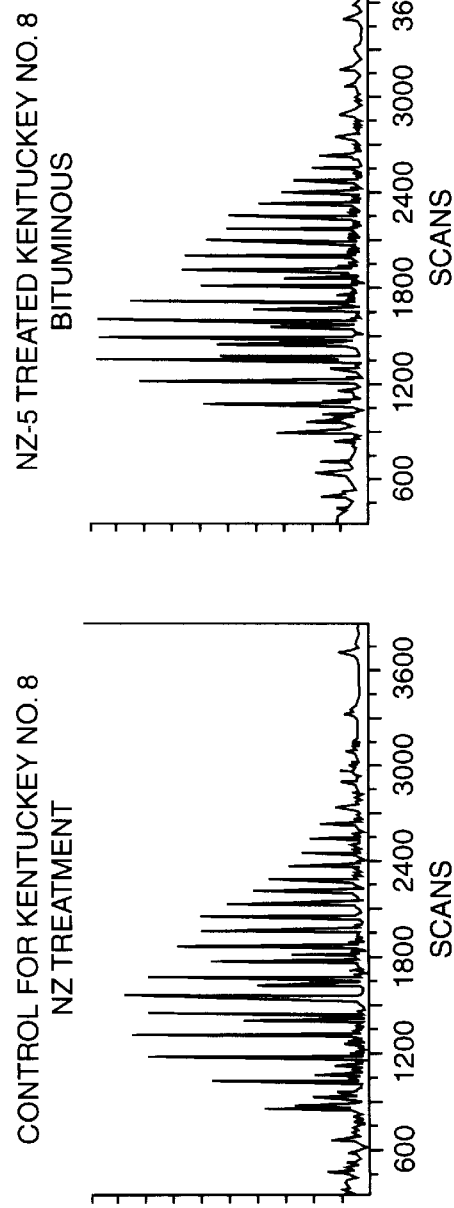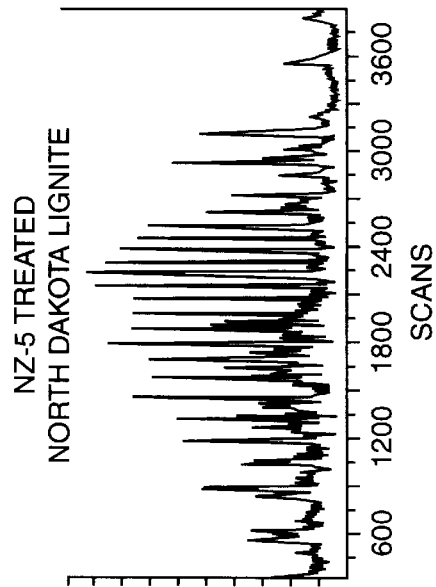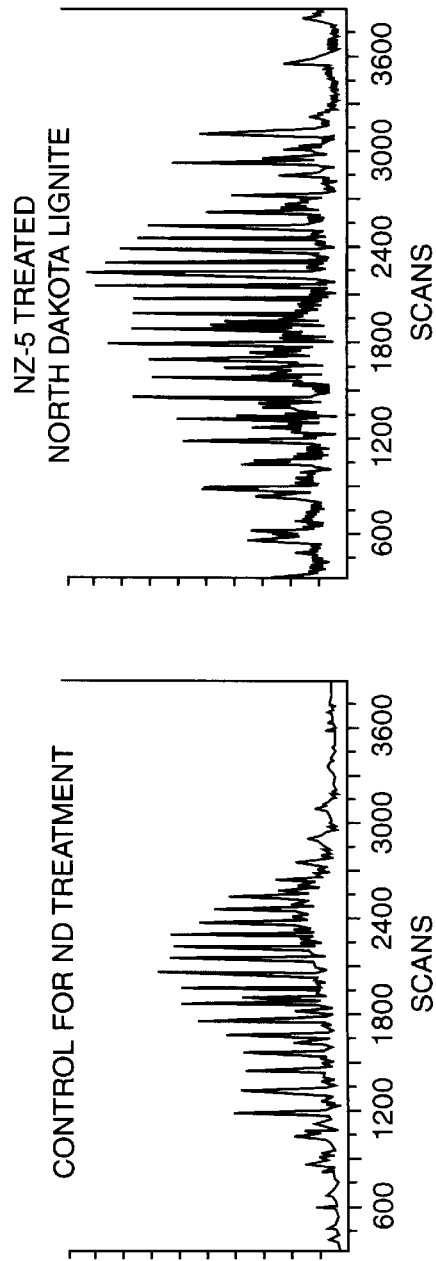

BIOCHEMICAL TRANSFORMATION OF COALS

CROSS-REFERENCE TO RELATED APPLICATIONS

The instant application is a continuation-in-part of application Ser. No. 08/169,417 filed Dec. 20, 1993, now abandoned, which is a divisional application of application Ser. No. 07/905,391 filed Jun. 29, 1992 now U.S. Pat. No. 5,297,625, which is a continuation-in-part of application Ser. No. 07/571,917 filed Aug. 24, 1990 and now abandoned.

This invention was made with government support under contract number DE-AC02-76CH00016, between the U.S. Department of Energy and Associated Universities, Inc. The government has certain rights in the invention.

BACKGROUND OF THE INVENTION

The present invention relates to biochemical transformation of solid carbonaceous material by a process of depolymerizing, desulfurizing and demineralizing using modified strains of thermophilic bacteria. More specifically, the present invention provides a process of treating an aqueous slurry of solid carbonaceous material, such as coal, with a culture of thermophilic bacteria which have been modified through challenge growth processes to be suitable for microbially enhanced oil recovery. Some of these bacteria were further adapted to grow on coal under challenged growth conditions and then utilized for biochemical transformation of solid carbonaceous material.

Coal is a solid carbonaceous material which is one of the most abundant fossil energy resources accessible to mankind. In terms of environmental protection, coal combustion is associated with significant problems, such as sulfur and nitrogen oxides emission, and the production of toxic metal containing ash. However, coal can be treated prior to combustion in a manner which reduces sulfur and ash contents. The treated product becomes a more suitable feedstock for combustion, liquefaction and gasification processes.

Sulfur appears in coal in three basic forms: as sulfates, pyrites and organic sulfur. Of the three forms, sulfates are the least significant, comprising less than 0.5 weight percent of coal. Pyritic and organic sulfur, however, may each constitute as much as 3.5 weight percent of the coal or from 40% weight to 60% weight of the total sulfur content, respectively. Thus, it is apparent that removal of an effective portion of inorganic and organic sulfur content prior to coal combustion could substantially reduce the emission of sulfur oxides into the atmosphere.

By organic sulfur is meant sulfur which is chemically bound within the coal matrix. Organic sulfur is present in four major forms. These are mercaptans or thiols, sulfides, disulfides and aromatic ring sulfur as exemplified by the thiophene system.

In the past, attempts have been made to alleviate the environmental problems associated with the combustion of coal. A number of processes for the treatment of coal ranging from ash and pyrite reduction to organic sulfur removal and coal liquefaction have been reported. These processes include numerous physical and mechanical techniques such as heavy media separation, elective agglomeration, flotation, jigging, magnetic, separation, leaching and hydrosulfurization. Problems associated with these developing technologies include reproductivity, slow kinetics and scale-up difficulties.

The removal of inorganic sulfur from pyrite is relatively easily accomplished by treatment with dilute nitric acid. The removal of organic sulfur, however, has not met with the same success. In recent years in order to obtain cleaner coal, coal has been subjected to biochemical processes wherein inorganic sulfur and minerals are removed through the action of several microorganisms belonging to the *Thiobacillus, Sulfolobus* and *Pseudomonas Clostridium* species. For example, U.S. Pat. No. 4,632,906 to Kopacz discloses a process for biodesulfurization by contacting carbonaceous material with *Bacillus Sulfasportate* of ATCC No. 39909. A mutant of the family Bacillaceae, this microorganism grows in a range between 15° C. to 30° C. and is not a thermophile. The background of the invention of the '906 disclosure describes *Sulfolobus Acidocaldarius*, a thermophilic sulfur and iron oxidizing microorganism which is a facultative autotroph. This organism has been used for removal of primarily pyritic sulfur from coal.

U.S. Pat. No. 4,206,288 to Detz et al. discloses a process for removal of pyritic sulfur from coal by microbial desulfurization of coal slurry with iron and sulfur oxidizing microorganisms selected from the *Thiobacillus ferooxidans* species. The microorganisms described in the '288 disclosure must be kept in a range of about 10° C. to 35° C. and are not thermophilic as required by the process of the present invention. Thus, they cannot be used at elevated temperatures.

U.S. Pat. No. 4,562,156 to Isbister et al. describes a mutant microorganism *Pseudomonas sp.* CB1 (ATCC 39381) used in the removal of organic sulfur compounds from carbonaceous materials including coal. In addition, the '156 disclosure describes other genera of microorganisms such as Arthrobacter and Acinetobacter used for microbiological treatment of petroleum and coal. These microorganisms are not thermophiles because they cannot grow at 41° C.

Generally, the microorganisms described in the above disclosures are not resistant to challenged environments, namely those including elevated temperatures, pressures, low pH, high levels of salinity and toxic metals. Frequently, it has been found more economical to process coal under elevated temperatures and pressures. Moreover, many types of coal have high toxic metal content which can kill many strains of bacteria even those which have been previously environmentally challenged.

Accordingly, there is a need in the art of biochemical transformation of solid carbonaceous materials for microorganisms which can depolymerize, desulfurize and/or demineralize solid carbonaceous material such as coal under environmentally challenged conditions.

It is therefore, an object of the present invention to provide modified thermophilic bacteria which are useful for the biochemical transformation of coals in a challenged environment.

SUMMARY OF THE INVENTION

The present invention, which addresses the needs of the prior art, provides a method of biochemically transforming complex macromolecular compounds found in solid carbonaceous materials, such as coal. More specifically, coal is treated with a biological treatment medium including strains of bacteria which have been metabolically weaned under challenged conditions to metabolize the complex macromolecular compounds found in coal thus providing a solid carbonaceous material which has been depolymerized, desulfurized and/or demineralized.

The biological treatment medium is prepared by nutritionally stressing thermophilic microorganisms to metabolize initially a non-solid carbonaceous material, such as crude oil at a desired temperature, pressure, pH and salinity.

The strains which survive in the presence of crude oil are then subjected to further challenge by selection under more extreme conditions. The selection process proceeds by the removal of the more easily metabolizable carbon sources while stepwise increasing the temperature, pressure, salinity and pH. The resulting modified or metabolically weaned thermophilic bacteria exhibit different chemical and biochemical properties than the thermophilic bacterial strains initially isolated from unique geothermal locations in the South Pacific and North America. Microorganisms which survive essentially on oil under extreme conditions of temperature, pressure, salinity and pH include *Achromobacter sp.* BNL-4-23 (ATCC 55021), *Sulfolobus solfataricus* BNL-TH-29 (ATCC 55022), *Sulfolobus solfataricus* BNL-TH-31 (ATCC 55023), *Sulfolobus acidocaldarius* BNL-TH-1 (ATCC 35091), *Pseudomonas sp.* BNL-4-24 (ATCC 55024), *Leptospirillum ferrooxidans* BNL-5-30 (ATCC 53992), *Leptospirillum ferrooxidans* BNL-5-31 (ATCC 53993), *Acinetobacter calcoaceticus* BNL-4-21 (ATCC 53996), *Arthrobacter sp.* BNL-4-22 (ATCC 53997).

The microorganisms which can feed on essentially crude oil are then isolated and are further nutritionally stressed to metabolize complex macromolecular compounds found in solid carbonaceous material such as coal. The nutritional stressing on a coal substrate is also conducted stepwise under challenged growth conditions including a temperature range from about 40° C. to about 85° C. reaction range pressure range from about ambient pressure to about 2500 p.s.i., a pH range from about 2 to about 10, a salinity range from about 1.5 weight % to about 35 weight % and a toxic metal concentration from about 0.01 weight % to about 10 weight %.

Microorganisms which can survive essentially on solid carbonaceous material such as coal under challenge growth conditions include *Acinetobacter calcoaceticus*, BNL-4-21s (ATCC 55489), *Arthrobacter sp.* BNL-4-22s (ATCC 55490), *Achromobacter sp.* BNL-4-23s (ATCC 55491), *Pseudomonas sp.* BNL-4-24s (ATCC 55492), Mixed Culture R.I.-1 (ATCC 55501), *Leptospirillum ferrooxidans* BNL-5-30s (ATCC 55523), *Leptospirillum ferroxidans* BNL-5-31s (ATCC 55524), *Thiobacillus ferroxidans* BNL-2-44s (ATCC 55525), *Thiobacillus ferrooxidans* BNL-2-45s (ATCC 55526), *Thiobacillus ferrooxidans* BNL-2-46s (ATCC 55527), *Thiobacillus ferrooxidans* BNL-2-47s (ATCC 55528), *Thiobacillus ferrooxidans* BNL-2-48s (ATCC 55529), *Thiobacillus ferrooxidans* BNL-2-49s (ATCC 55530), Unknown BNL-NZ-3 (ATCC 55488), Unknown BNL-NZ-5 (ATCC to be determined), Mixed Culture R.I.-2 (ATCC 55502), Mixed Culture R.I.-3 (ATCC 55503), Mixed Culture R.I.-4 (ATCC 55504), Mixed Culture R.I.-5 (ATCC 55505), Mixed Culture R.I.-6 (ATCC 55506), Mixed Culture R.I.-7 (ATCC 55507), Mixed Culture R.I.-8 (ATCC 55508), Mixed Culture R.I.-9 (ATCC 55509), Mixed Culture R.I.-10 (ATCC 55510), Mixed Culture R.I.-11 (ATCC 55511), Mixed Culture R.I.-12 (ATCC 55512), Mixed Culture R.I.-13 (ATCC 55513), Mixed Culture R.I.-14 (ATCC 5554) and mixtures thereof.

The modified microorganisms metabolically weaned by nutritional stressing under challenged growth conditions are also encompassed in the present invention.

As a result of the present invention a process for the biochemical transformation of solid carbonaceous material is provided which can be used very effectively to break down the complex hydrocarbon structure of coal to provide a biochemically transformed coal which is cleaner and richer in low molecular weight hydrocarbon fragments. The biotransformed coal is a more suitable feedstock for liquefaction, gasification and/or combustion processes. The metabolically weaned microorganisms of the present invention are capable of cleaving selectively macromolecular compounds found in solid carbonaceous materials at hetero atom sites thereby providing a coal which has been depolymerized, desulfurized and demineralized. As a result, the biochemically transformed coal obtained by applying the process of the present invention also lowers operation costs of coal liquefaction, gasification, combustion and other coal utilizations.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

FIG. 3 is a pyrolysis-gas chromatography-mass spectroscopy analysis of alkanes for Kentucky No. 8 bituminous coal and North Dakota lignite, untreated and treated with modified strains BNL-NZ-5 bacteria.

DEPOSIT

A number of biologically pure microorganisms, modified following the procedures of the present invention and illustrative of the modified thermophilic microorganisms useful in the process of the present invention have been deposited in the American Type Culture Collection 10801 University Boulevard, Manassas, Va. 20110-2209 prior to the filing date of this application in accordance with the permanency and accessibility requirements of the U.S. Patent and Trademark Office. The following is a list of the deposited microorganisms:

| Scientific Description | Applicants' Reference | ATCC Designation |
| --- | --- | --- |
| Achromobacter sp. | BNL-4-23 | 55021 |
| *Sulfolobus solfataricus* | BNL-TH-29 | 55022 |
| *Sulfolobus solfataricus* | BNL-TH-31 | 55023 |
| Pseudomonas sp. | BNL-4-24 | 55024 |
| *Leptospirillum ferrooxidans* | BNL-5-30 | 53992 |
| *Leptospirillum ferrooxidans* | BNL-5-31 | 53993 |
| *Acinetobacter calcoaceticus* | BNL-4-21 | 53996 |
| Arthrobacter sp. | BNL-4-22 | 53997 |
| Acinetobacter calcoaceticus | BNL-4-21s | 55489 |
| Arthrobacter sp. | BNL-4-22s | 55490 |
| Achromobacter sp. | BNL-4-23s | 55491 |
| Pseudomonas sp. | BNL-4-24s | 55492 |
| *Leptospirillum ferrooxidans* | BNL-5-30s | 55523 |

-continued

| Scientific Description | Applicants' Reference | ATCC Designation |
|---|---|---|
| *Leptospirillum ferroxidans* | BNL-5-31s | 55524 |
| *Thiobacillus ferroxidans* | BNL-2-44s | 55525 |
| *Thiobacillus ferrooxidans* | BNL-2-45s | 55526 |
| *Thiobacillus ferrooxidans* | BNL-2-46s | 55527 |
| *Thiobacillus ferrooxidans* | BNL-2-47s | 55528 |
| *Thiobacillus ferrooxidans* | BNL-2-48s | 55529 |
| *Thiobacillus ferrooxidans* | BNL-2-49s | 55530 |
| Unknown | BNL-NZ-3 | 55488 |
| Unknown | BNL-NZ-5 | to be determined |
| Mixed Culture | R.I.-1 | 55501 |
| Mixed Culture | R.I.-2 | 55502 |
| Mixed Culture | R.I.-3 | 55503 |
| Mixed Culture | R.I.-4 | 55504 |
| Mixed Culture | R.I.-5 | 55505 |
| Mixed Culture | R.I.-6 | 55506 |
| Mixed Culture | R.I.-7 | 55507 |
| Mixed Culture | R.I.-8 | 55508 |
| Mixed Culture | R.I.-9 | 55509 |
| Mixed Culture | R.I.-10 | 55510 |
| Mixed Culture | R.I.-11 | 55511 |
| Mixed Culture | R.I.-12 | 55512 |
| Mixed Culture | R.I.-13 | 55513 |
| Mixed Culture | R.I.-14 | 55514 |

DETAILED DESCRIPTION OF THE INVENTION

The present invention provides a method for the biochemical transformation of solid carbonaceous material. More specifically, the method includes treating a slurry of coal with modified biological pure strains of thermophilic microorganisms which are capable of depolymerizing, desulfurizing and/or demineralizing coal by selectively cleaving molecular structures at organic carbon-carbon sites, carbon-sulfur sites and other hetero-atom sites including metals and nitrogen.

Figure 1:
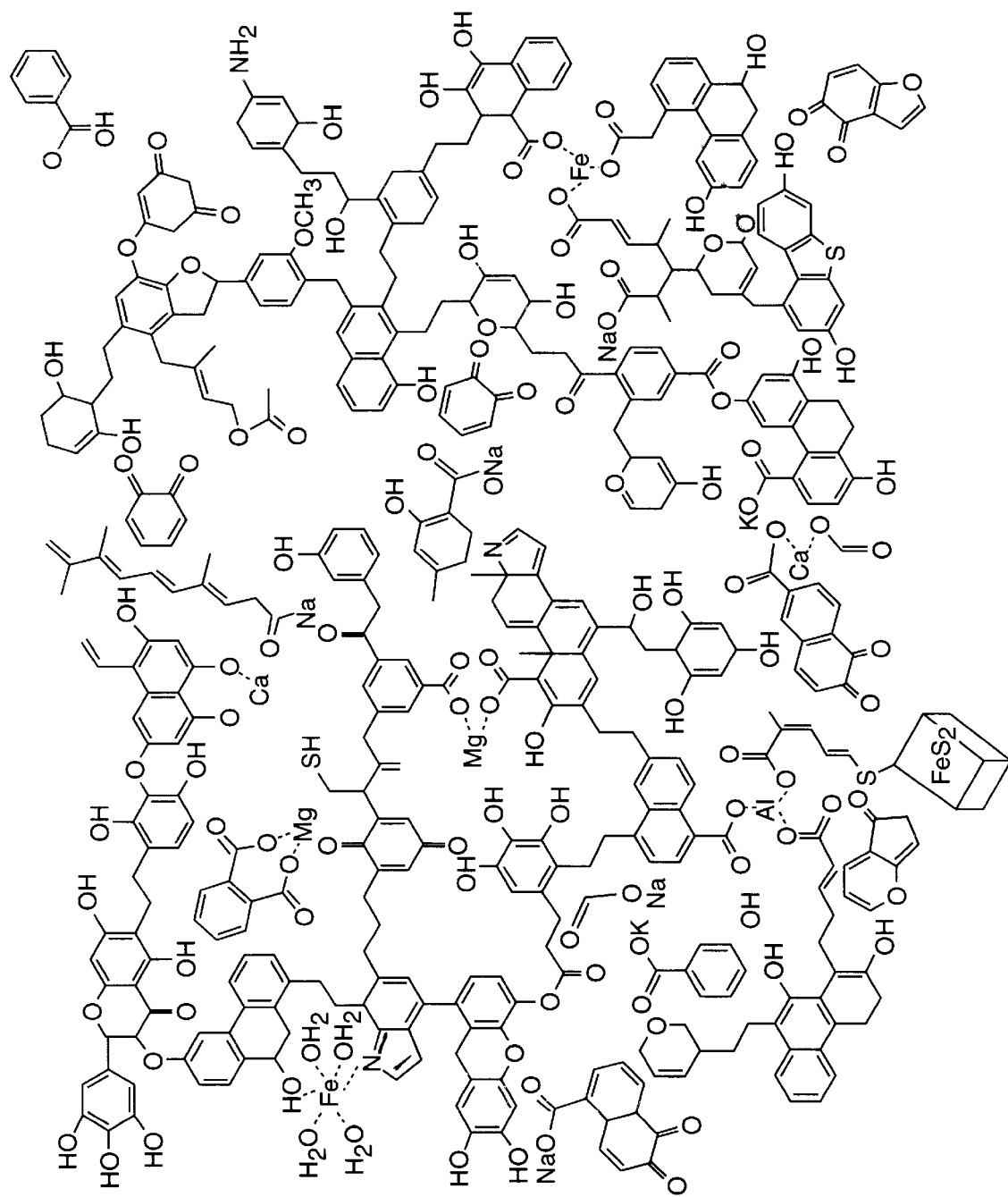
FIG. 1 illustrates a typical chemical structure of bituminous coal.

In the complex polymeric structure of coals, organic sulfur is believed to be bound primarily in crosslinked thiophenic rings, thiols, sulfides, disulfides bridges, and sulfones. The complex coal structure frequently encloses pyrites, sulfates, and elemental sulfur. A typical chemical structure of bituminous coal is shown in FIG. 1.

"Metabolically weaned" as used in the present invention refers to the microorganism or microorganisms which have been adapted to metabolize solid complex macromolecular compounds found in solid carbonaceous materials. This metabolization includes, for example, depolymerization, desulfurization, and demineralization of solid carbonaceous materials such as coal.

As used in the present invention depolymerization refers to the decomposition of complex macromolecular compounds found in solid carbonaceous materials to lower molecular weight hydrocarbons residues. Desulfurization refers to the removal of sulfur from complex macromolecular compounds found in solid carbonaceous material. Desulfurization also results in the formation of hydrocarbons of lower molecular weight and other simpler organic compounds. Demineralization is used to refer to the removal of trace metals by microorganisms capable of metabolizing organometallic compounds found in solid carbonaceous materials. Thus, the result of biochemical treatment of solid carbonaceous material, such as coal, with the challenged microorganisms of the present invention is a coal matrix which has simpler hydrocarbons and is lower in sulfur and toxic metal content. The resulting transformed matrix undergoes combustion, liquefaction, or gasification much more efficiently and with the formation of fewer environmentally undesirable byproducts.

The biochemical transformation process of the present invention is broadly applicable to the treatment of various types of sulfur-containing solid carbonaceous material. One type of sulfur-containing solid carbonaceous material is coal. Coals which can be treated by the process of the present invention include anthracite, bituminous, subbituminous, mine tailings, fines, lignite and the like. Other finely divided solid carbonaceous solids, such as coke may also benefit from the present process. Preferably, the coal subjected to the present biochemical transformation process is present as a slurry in a particulate form. Thus, in carrying out a preferred embodiment of the present invention, typically raw mined coal is first reduced to a smaller particle size preferably less than but not limited to about 100 mesh. The coal particulates are then formed into a slurry with water such that the solids concentration in the slurry is from about 1% to about 60% by weight.

In a preferred embodiment, the slurry of the carbonaceous material includes bituminous Kentucky No. 8 coal and/or North Dakota lignite. The elemental analysis for North Dakota lignite and Kentucky No. 8 bituminous coal is set forth in Table 1 below.

TABLE 1

Elemental Analysis of Coal

|  | North Dakota lignite | Kentucky No. 8 bituminous |
|---|---|---|
| Carbon | 61.08 | 78.3 |
| Hydrogen | 4.08 | 3.3 |
| Oxygen* | 23.44 | 4.6 |
| Nitrogen | 0.87 | 1.8 |
| Sulfur | 0.53 | 1.1 |
| Ash | 10.00 | 10.095 |

*By difference

In accordance with the present invention, modified microorganisms are produced for use in biochemical transformation of solid carbonaceous material. Selected thermophilic microbial strains isolated from unique geothermal locations in the South Pacific and North America are metabolically weaned and forced to adapt to growth on an oil substrate at a desired temperature, pressure, pH and salinity. The thermophilic bacteria which survive growth on an essentially oil substrate are then adapted to grow on a solid carbonaceous material substrate, such as coal at a desired temperature, pressure, pH, salinity and toxic metal concentration.

An aqueous coal slurry is inoculated with modified strains of selected microorganisms. A nutrient medium is generally added to the aqueous slurry in order to provide the source of metabolites. A typical nutrient medium comprises sodium chloride, potassium phosphate, magnesium sulfate and a source of casein. The temperature at which the biochemical transformation process is carried out is generally in a range from about 40° C. to about 85° C. The pH is maintained in a range from about 2 to about 10. A final pH of about 4 is preferred. The pressure range is maintained from about ambient to about 2500 p.s.i. The modified strains used in the process of the present invention are adapted to toxic metal concentrations from about 0.01 weight % to about 10 weight %, depending on the metal. The strains useful for the biotreatment of carbonaceous material are also adapted to elevated concentrations of salinity from about 1.5 weight % to about 35 weight %.

The original microorganisms employed in the present invention have been isolated from geothermal sources and have been "metabolically weaned" to metabolize solid carbonaceous material. Just as offspring must become accustomed to food other than maternal nourishment, thermophilic microorganisms are grown in a challenged environment so that they are forced to adapt to metabolizing solid carbonaceous material. After the microorganisms have been isolated, they are initially grown in a medium containing crude oil supplemented with other sources of nutrients, such as minerals and more easily metabolized sources of energy such as molasses and yeast extract. The strains which can survive in the presence of crude oil are then nutritionally stressed by subjecting them to further challenge by selection under more extreme conditions.

"Nutritionally stressing" as used in the present invention means to forcedly adapt the microorganism to metabolize a source of nutrition which it does not normally metabolize during growth. This has been accomplished with respect to the present invention by a "challenged growth" process. The selection processes proceed by removal of the more easily metabolizable carbon sources, i.e., the molasses, yeast extract, oil and the like while increasing stepwise the concentration of coal and anyone of the other conditions such as temperature, pressure, pH, salinity and toxic metals content.

In a challenged growth process the thermophilic microbial strain or strains are grown in a medium containing crude oil supplemented with carbon sources other than carbonaceous materials and nutrients other than crude oil at a selected temperature, pressure and salinity concentration. The surviving thermophilic microbial strains are isolated and grown in a medium containing increased amounts of crude oil and decreasing amounts of the carbon source which is other than the carbonaceous materials at a temperature, pressure and salinity higher than in the previous step. The previous step is then repeated and in each successive step the medium contains increased amounts of crude oil and decreasing amounts of the carbon source which is other than carbonaceous materials and at a temperature, pressure and salinity higher than in each previous step until microbial strains are obtained that are capable of growing essentially on crude oil as a carbon source and at a temperature range from about 40° C. to about 85° C. at a pressure range from about ambient to about 2500 p.s.i. and the salinity range from about 1.3 weight % to about 35 weight %. The thermophilic microbial strains which are able to survive growth on essentially crude oil are then selected and grown in a medium containing decreasing amounts of oil and increasing amounts of coal as a carbon source at a first chosen condition selected from the group consisting of temperature, pressure, pH, salinity and toxic metal concentration, wherein the chosen condition is higher than in the previous step. The nutritional stressing on coal is repeated until the medium contains a higher amount of coal as a carbon source at a successive chosen condition higher than in the previous step until the microbial strain or mixture of microbial strains is developed which is capable of growing on essentially coal as a carbon source and at a final chosen condition selected from the group consisting of temperature, pressure, pH, salinity and a toxic metal concentration. The challenged growth temperature for nutritional stressing on a coal substrate is from about 40° C. to about 85° C., the pressure is from about ambient to about 2500 p.s.i., pH is from about 2 to about 10, the salinity is from about 1.5 weight % to about 35 weight % and the toxic metal concentration is from about 0.01% weight % to about 10% weight %. Methods of isolation and culturing have been described in detail in U.S. application Ser. No. 571,917 filed Aug. 24, 1990 now abandoned and U.S. application Ser. No. 905,391 filed Jun. 29, 1992 which has issued U.S. Pat. No. 5,297,625, the contents of which are incorporated herein by reference as if set forth in full. Thus, the microorganisms of the present invention are metabolically weaned to metabolize solid carbonaceous material under challenged growth conditions.

In addition to thermophilic bacteria strains which have been engineered to survive a harsh variety of environmental conditions present in oil reservoirs and which have been useful in microbially enhanced oil recovery ("MEOR"), other strains of thermophilic bacteria have been developed which have been useful for the biochemical transformation of solid carbonaceous materials, such as coal. As used in the present invention, thermophilic bacteria refer to bacteria which thrive at temperatures exceeding 40° C.

Table 2, which follows, lists biologically pure strains of thermophilic bacteria produced through challenged growth processes, which modified microorganisms are useful for biochemical transformation of carbonaceous material including oil and coal. In Column "a" of table 2 there are listed the cultures which were subjected to challenged growth processes by the source of the original culture. In column "b" the American Type Culture Collection No. or "ATCC No." is set forth. In column "c" the Brookhaven National Laboratory No. or "BNL No." is listed.

TABLE 2

Microorganisms Produced Through Challenged Growth

| (a)<br>Origirial Culture<br>Designation<br>Scientific Description | (b)<br>Source/<br>Depository<br>ATCC NO. | (c)<br>Modified<br>Microorganism<br>BNL No. |
|---|---|---|
| 1. Achromobacter sp. | 55021 | BNL-4-23 |
| 2. Sulfolobus solfataricus | 55022 | BNL-TH-29 |
| 3. Sulfolobus solfataricus | 55023 | BNL-TH-31 |
| 4. Pseudomonas sp. | 55024 | BNL-4-24 |
| 5. Leptospirillum ferrooxidans | 53992 | BNL-5-30 |
| 6. Leptospirillum ferrooxidans | 53993 | BNL-5-31 |
| 7. Acinetobacter calcoaceticus | 53996 | BNL-4-21 |
| 8. Arthrobacter sp. | 53997 | BNL-4-22 |
| 9. Arthrobacter sp. | 55490 | BNL-4-22s |
| 10. Achromobacter sp. | 55491 | BNL-4-23s |
| 11. Pseudomonas sp. | 55492 | BNL-4-24s |
| 12. Leptospirillum ferrooxidans | 55523 | BNL-5-30s |
| 13. Leptospirillum ferroxidans | 55524 | BNL-5-31s |
| 14. Thiobacillus ferroxidans | 55525 | BNL-2-44s |
| 15. Thiobaciilus ferrooxidans | 55526 | BNL-2-45s |
| 16. Thiobaciilus ferrooxidans | 55527 | BNL-2-46s |
| 17. Thiobacillus ferrooxidans | 55528 | BNL-2-47s |
| 18. Thiobacilius ferrooxidans | 55529 | BNL-2-48s |
| 19. Thiobacillus ferrooxidans | 55530 | BNL-2-49s |
| 20. Unknown | 55488 | BNL-NZ-3 |
| 21. Unknown | to be determined | BNL-NZ-5 |
| 22. Mixed Culture | 55501 | R.I.-1 |
| 23. Mixed Culture | 55502 | R.I.-2 |
| 24. Mixed Culture | 55503 | R.I.-3 |
| 25. Mixed Culture | 55504 | R.I.-4 |
| 26. Mixed Culture | 55505 | R.I.-5 |
| 27. Mixed Culture | 55506 | R.I.-6 |
| 28. Mixed Culture | 55507 | R.I.-7 |
| 29. Mixed Culture | 55508 | R.I.-8 |
| 30. Mixed Culture | 55509 | R.I.-9 |
| 31. Mixed Culture | 55510 | R.I.-10 |
| 32. Mixed Culture | 55511 | R.I.-11 |
| 33. Mixed Culture | 55512 | R.I.-12 |
| 34. Mixed Culture | 55513 | R.I.-13 |
| 35. Mixed Culture | 55514 | R.I.-14 |

<sub></sub>

From the modified microorganisms listed in Table 2 the first eight, namely BNL-4-23, BNL-TH-29, BNL-TH-31, BNL-4-24, BNL-5-30, BNL-5-31, BNL-4-21, BNL-4-22 have been challenged or adapted on oil substrates and increasing temperatures, pressures, pH and salinity as set forth in U.S. application bearing Ser. No. 08/169,147, which is issued as U.S. Pat. No. 5,492,828 the contents of which are incorporated herein by references as if set forth in full. The remaining microorganisms listed in Table 2, have been initially challenged on crude oil substrates, and then have been adapted in successive steps in media containing decreasing amounts of crude oil and increasing amounts of coal at selected conditions chosen from temperature, pressure, salinity, pH and toxic metal content wherein each successive selected condition is higher than in the previous step. For example, the salinity is gradually increased from about 1.5 weight % to about 35 weight %, wherein 15% weight is preferred.

The biochemical treatment of carbonaceous material can be caused by a single biologically pure strain of modified microorganism or mixed cultures of mutated biologically pure microorganisms which are used subsequently under either aerobic or anaerobic conditions depending on the ranges of salinity, toxic metals concentrations, pH, temperatures and pressures present when the solid carbonaceous material is treated. It is possible to maximize the effect of the biochemical transformation of solid carbonaceous material by using a combination of organisms, wherein each of which is very efficient in producing one or more of the desired degradations. For example, a mixed culture could include modified organisms which cleave the coal matrix very efficiently at heterosites, thereby causing the depolymerization to lighter hydrocarbons. The same mixture could include modified organisms which are efficient at desulfurizing and/or demineralizing of the coal matrix. The mixed culture approach permits tailoring of the microbial package used for biochemical transformation of different types of solid carbonaceous material.

For the purposes of the present invention, the preferred microorganisms are the thermophilic archaebacteria of the Sulfolabus species which have been modified by challenged growth processes. Most preferred are BNL-TH-29, BNL-NZ-3 and BNL-NZ-5 which were obtained from the parent strains of *Sulfolabus Solfataricus* (ATCC 35091), Unknown (ATCC 55488) and Unknown (ATCC to be determined). These modified bacterial strains are especially suitable for the processes of the present invention because they remain viable over extended periods, often up to six (6) months under harsh environmental conditions including temperatures in a range of 40° C. to about 85° C., high pressures in a range from about ambient to about 2500 p.s.i., pH range from about 2 to about 10, toxic metal concentration in a range from about 0.01 wt % to about 10 wt %, and salinity in a range from about 1.5 wt % to about 35 wt %.

Analysis of the solid carbonaceous material treated with the modified microorganisms of the present invention at a temperature range of from about 40° C. to about 85° C. and a pressure range of ambient-2500 p.s.i. indicates that as a result of biotreatment, the carbonaceous material becomes depolymerized and desulfurized and shows significantly decreased trace metal content.

In the examples which follow, bioreactors were used for metabolically weaning the microorganisms by challenged growth procedures in a 40°-85° C. water bath at total pressures ranging from ambient to 2500 p.s.i., under carbon dioxide and nitrogen in a volume ratio of 1:25, at 70° C. Minibioreactors are used for anaerobic pressurized experiments while conventional culture flasks are used for aerobic experiments at elevated temperatures.

The medium for the challenged growth procedures includes inorganic salts, e.g., $(NH_4)_2SO_4$, $MgSO_4$, $KH_2PO_4$, crude oil, yeast extract and coal as a source of carbon. Incubations of cultures can be carried out under different pressures, gas compositions and temperatures. Yeasts, molasses and sources of carbons other than crude oil are used in conjunction with crude oil only at initial stages of growth. The organism is allowed to grow to a steady concentration, i.e. $1\times10^8$/ml under conditions in which the concentration of oil is increased and the other sources of carbon are decreased. During this initial stage, the organism is maintained at elevated temperatures and pressures. Generally, if the organism grows successfully to the desired level in the presence of crude oil as the sole source of carbon, but only at ambient temperatures, then it is "challenged" stepwise to higher temperatures and pressures until steady growth and desired concentrations are achieved. Two or three transfers at optimum conditions of growth often suffice to generate a modified microorganism suitable for microbially enhanced oil recovery ("MEOR").

The modified microorganisms challenged as described above are then isolated and further adapted to growth on coal, increased salinity and toxic metal content. This process is accomplished by incubating the microorganisms suitable for MEOR in media of decreasing oil and increasing coal concentration as a source of carbon and such toxic metals as ordinarily found in coal. This process is also accomplished in stepwise manner, i.e., when the organism grows successfully in the presence of coal as the sole source of carbon, but only at ambient temperatures, then it is further "challenged" stepwise to higher temperatures, pressures, salinity and toxic metal contraction until steady growth and desired concentrations are achieved. Thus, the temperature is increased from about 40° C. to about 85° C. The pressure is increased from about ambient to about 2500 p.s.i. The pH is increased from about 2 to about 10. The salinity is also increased from about 1.5 wt % to about 35 wt % sodium chloride, wherein a concentration of 15% by weight is preferred. The toxic metal content is increased from about 0.01 wt % to about 10 wt %, depending on the metal.

The determination of organic sulfur content of coal is conventionally measured as the difference between total sulfur and inorganic sulfur. The results are often subject to large errors inherent to the method used for the determination of elemental sulfur, sulfate and pyrite in coal. More recently, pyrolysis-gas chromatography-mass spectroscopy ("PY-GC-MS") and x-ray absorption near edge structure spectroscopy ("XANES") have been used as sensitive analytical tools for the determination of organically bound sulfur in kerogen and asphaltenes which chemically resemble coal. In the present invention, untreated and biotreated coal samples have been analyzed first by PY-GC-MS and then by XANES methods.

Figure 2:
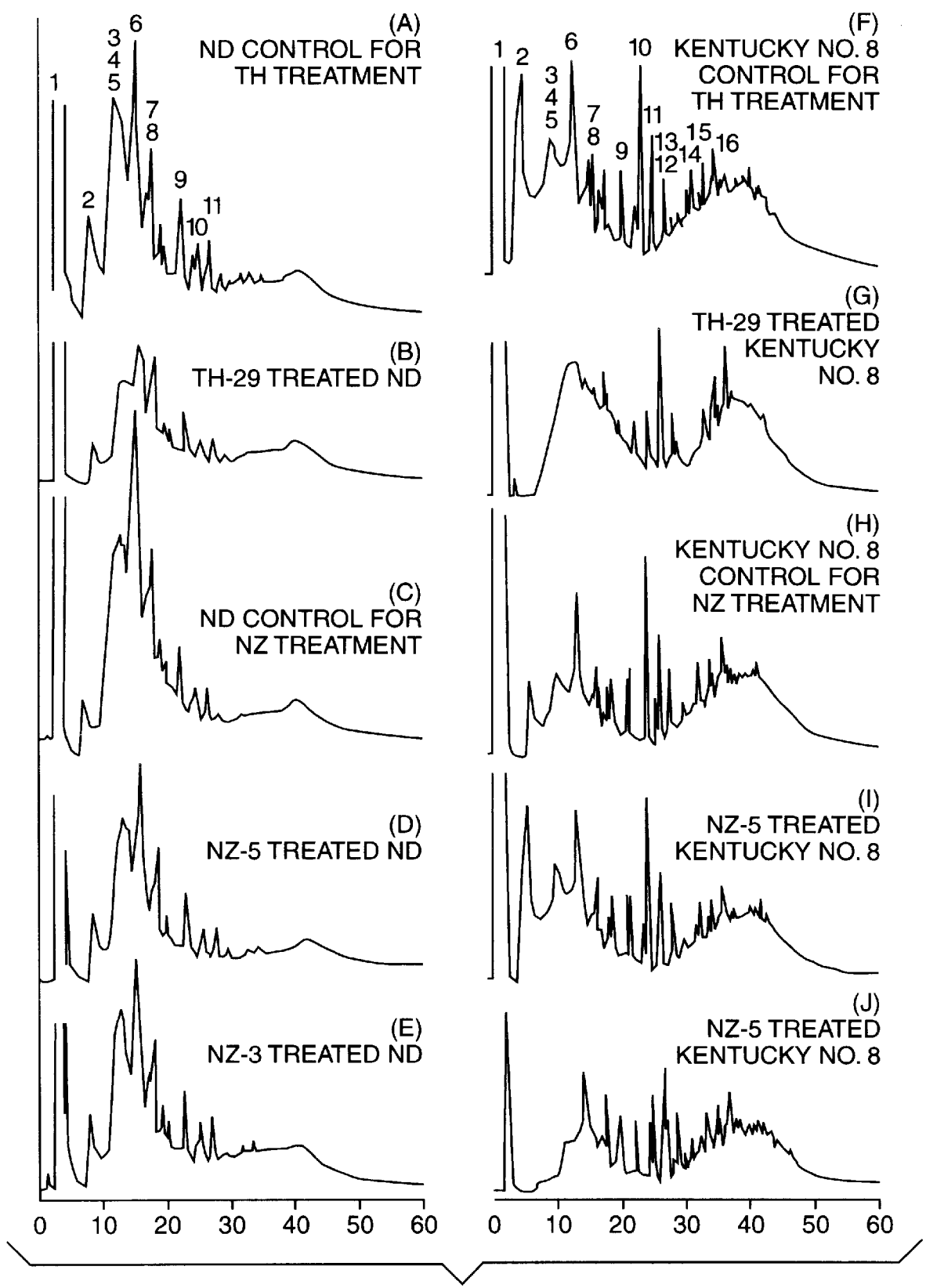
FIG. 2 is a pyrolysis-gas chromatography-photometric detector analysis of sulfur content for North Dakota lignite and Kentucky No. 8 coal untreated and treated with modified strains of BNL-TH-29, BNL-NZ-3 and BNL-NZ-5 bacteria.

In the examples which follow, the efficacy of the present invention is clearly shown. Two independent analytical methods were used to analyze coal which has undergone biochemical transformation in accordance with the process of the present invention. These analytical methods are pyrolysis-gas chromatography mass spectrometry ("PY-GC-MS") and x-ray absorption near edge structure spectroscopy ("XANES"). For example, as shown in FIG. 2 and Table 4 herein an analysis of biochemically transformed lignite and bituminous coals treated with modified, biologically pure thermophilic bacteria BNL-TH-29, BNL-NZ-3 and BNL-NZ-5 shows a reduction of the sulfide content and the content of C1 to C5 substituted thiophenes. In addition, as shown in FIG. 3 hereto PY-GC-MS analysis of biotreated and untreated bituminous coal indicates that during the biochemical treatment of coal a biochemical transformation takes place during which the molecular structure of coal is cleaved at hetero atom sites such as sulfur, nitrogen and metals so that the treated coal contains more small to medium molecular weight fractions in preference to high molecular weight residues. In terms of scan numbers (low number, e.g. 600, corresponds to molecular weights of about C6 to C10 hydrocarbons compounds and progressively increasing reaching a molecular weight range of above C30 hydrocarbons corresponding to the 3000 scan numbers). Without wishing to be bound by any theory it appears that during biotreatment of solid carbonaceous material, the overall breakage of sulfide linkages leads to an extensive breakdown of crosslinking in the structure of the carbonaceous material.

During the biochemical transformation of coal the removal of organic sulfur is often accompanied by the removal of amounts of trace metals. The trace metals found in coal are often toxic. Metals removed by biochemical treatment of coals include vanadium, manganese, copper, strontium, yttrium, zirconium, lanthanum, cerium, lead, thorium and uranium.

EXAMPLES

The following examples have been carried out to show the effect of different strains of modified microorganisms on solid carbonaceous material. These examples also serve to provide further appreciation of the invention but are not meant in any way to restrict the effective scope of the invention.

Example 1
Isolation and Culturing Methods of Thermophilic Bacteria

Thermophilic bacteria NZ and TH capable of hydrocarbon degradation were isolated from unique geothermal locations located in the South Pacific and North America, respectively. Because both cultures were isolated from geothermal sources, they grew well in temperatures ranging from 65° C. to 80° C. For example, a 5% (vol./vol.) inoculum reached stationary phase growth in two days at concentrations about $1 \times 10^8$ ml$^{-1}$.

The medium formula used for NZ was 1 g pancreatic digest casein, 0.05 g sodium thioglycollate, 2.5 g NaCl, 0.25 g CaCl$_2$, 1.57 g K$_2$HPO$_4$, 0.891 g KH$_2$PO$_4$, 0.4 g (NH$_4$)$_2$SO$_4$ and 0.25 g MgSO$_4$ in a liter of water. The formula for TH medium was 1 g yeast extract, 1 g casamino acids, 3.1 g KH$_2$PO$_4$, 2.5 g (NH$_4$)$_2$SO$_4$, 0.2 g MgSO$_4 \cdot$7H$_2$O, 0.25 g CaCl$_2$2H$_2$O, 0.22 mg ZnSO$_4$7H$_2$O, 0.05 mg CuCl$_2$2H$_2$O, 0.03 mg Na$_2$MoO$_4$2H$_2$O, 0.03 mg VOSO$_4$2H$_2$O and 0.01 mg CaSO$_4$7H$_2$O in a liter of distilled water. The final pH was adjusted to 4.0 by adding H$_2$SO$_4$. Three strains of gram positive rods from these isolates were used in this study. A detailed description of isolation and culturing methods for thermophilic NZ and TH bacteria is set forth in commonly-owned U.S. application bearing Ser. No. 07/905,391 filed Jun. 29, 1992, the contents of which are incorporate herein as if set forth in full.

Example 2
Biotreatment of Coals

Powdered coals were stored in a desiccator without any special effort to sterilize samples prior to executing the experiments. Two per cent (w/v) of the powdered coal (100 mesh) was cultured with selected bacteria for a week in an Erlenmeyer flask without shaking at 65° C. Control samples were subject to identical culture conditions without, however, added bacterial inoculum. After treatment, the reaction mixtures were filtered through Whatman No. 1 filter paper and washed twice, each time submersing the filtered coal in 100 ml of distilled water per 2 g sample and shaken vigorously. The reaction mixtures were then filtered through Whatman No. 1 filter paper again. Finally, the samples were air dried and stored in a desiccator at room temperature. The samples were dried to constant weight for further analysis. About 2.5–3.0 mg of dried coal samples were analyzed by a Perkin-Elmer Model 240C elemental analyzer in accordance with procedures published in a report by Perkin-Elmer Instrument Co. entitled "CHN Analysis of Coal with the Perkin-Elmer Model 240 Elemental Analyzer and Sulfur Analysis Kit for the Model 240 Elemental Analyzer, Report No. 993-9417, Danbury, Conn., 1980. The analyses involving coal with 1%, or less, sulfur content were calibrated against standards and untreated coal as illustrated in Table 3 below. The results were reported as averages of triplicate measurements.

TABLE 3

TOTAL SULFUR REMOVAL (%)

| TREATMENT | NORTH DAKOTA LIGNITE COAL | KENTUCKY NO. 8 BITUMINOUS COAL |
|---|---|---|
| 1. Control (a) (Inorganic sulfur removal) | 11 ± 2 | 10 ± 1 |
| 2. BNL-NZ-3 (Both Inorgariic and Organic Sulfur Removal) | 18 ± 3 | 12 ± 1 |
| 3. Organic Sulfur Removal by BNL-NZ-3 = 2-1 | 7 ± 2 | 2 ± 1 |
| 4. BNL-NZ-5(Both Inorganic and Organic Sulfur Removal) | 24 ± 3 | 25 ± 2 |
| 5. Organic Sulfur Removal by BNL-NZ-5 = 4-1 | 13 ± 2 | 15 ± 2 |
| 6. Control (b) (Inorganic Sulfur Removal) | 19 ± 3 | 20 ± 2 |
| 7. BNL-TH-29 (Both Inorganic and Organic Sulfur Removal) | 29 ± 4 | 30 ± 2 |
| 8. Organic Sulfur Removal BNL-TH-29 = 7-6 | 10 ± 3 | 10 ± 2 |

(a) (b) The difference in sulfur removal values for controls is due to different media used for the growth of organisms. The media for control (b) was more acidic than for control (a) and therefore more inorganic sulfur was also removed.

The results set forth in Table 3 show that the biotreatment of bituminous coal No. 8 from Kentucky and lignite coal from North Dakota with biologically pure thermophilic strains of BNL-TH-29, BNL-NZ-3, and BNL-NZ-5 resulted in a reduction of the total sulfur content. In comparison, there was a small reduction of sulfur content observed in the control experiments, which is attributed to the action of indigenous bacteria present in coal and the dissolution of inorganic sulfur forms such as sulfates at 65° C. The additional total sulfur reduction was substantial indicating that the process of the present invention is very effective for organic sulfur removal and as a result for coal desulfurization.

In another embodiment, prior to biotreatment, the coal sample is washed with dilute nitric acid to remove the inorganic sulfur. For example, dilute nitric acid treatment was used to remove pyrite and other forms of inorganic sulfur in coal. Coal samples of 10 g of 150–200 mesh were suspended in 100 ml of 2N nitric acid and kept at room temperature for 14 hours. The acid treated coals were then thoroughly washed with 200 ml of distilled water. They were then filtered, air dried, and kept in a desiccator at room temperature for further biotreatment.

Example 3
PY-CG-MS Analysis

About 2.00 mg desiccator dried coals as obtained in Example 2 were pyrolyzed in a stream of pure helium having less than 1 ppm air in a Chemical Data System model 190 pyroprobe. The pyroprobe was programmed at a heating rate of 10,000° C./sec to 660° C. for 20 seconds, and the pyrolysate was swept directly into a Perkin Elmer 8700 Gas Chromatograph ("GC") with a J & W DB-1 capillary column 30 mm in length, 0.25 mm I D and 1 μm film. The GC temperature program was 40° C. for 5 minutes which was then increased to 320° C. for 25 minutes at a heating rate of 8° C./minute. The GC system was equipped with a splitter which allowed the effluent leaving the column to be simultaneously analyzed by a Flame Photometric Detector (FPD) and by a mass selective Ion Trap Detector (ITD). The FPD was set on fast response and non-linearization mode, whereas the ITD was set on mass scan of 40 to 500 Daltons at a rate of one scan per second. The results are presented in FIGS. 2 and 3 hereto. The composition of the chromatogram were identified by the use of standards and by means of EPA/NIH mass spectrometric data base library search. Some of the peaks identified in FIG. 2 are listed in Table 4.

TABLE 4

Peaks listed in FIG. 2

| | |
|---|---|
| 1 | $H_2S$ and other sulfur gases |
| 2 | Thiophene |
| 3 | C1 substituted thiophenes |
| 4 | C4–C8 sulfides |
| 5 | C3–C6 mercaptans |
| 6 | Unidentified sulfur compounds |
| 7 | Unidentified sulfur compounds |
| 8 | C2 substituted thiophenes |
| 9 | C3 substituted thiophenes |
| 10 | C4 substituted thiophenes |
| 11 | C5 substituted thiophenes |
| 12 | Benzothiophenes |
| 13 | C1 substituted benzothiophenes |
| 14 | C2 substituted benzothiophenes |
| 15 | Bithiophenes |
| 16 | Dibenzothiophenes |

The peaks shown in FIG. 2 and identified in Table 4 indicate that the treatment of lignite coal with metabolically weaned thermophilic bacteria BNL-TH-29, BNL-NZ-3 and BNL-NZ-5 reduced sulfides and C1 to C5 substituted thiophenes. The results shown in FIG. 2 indicate substantial degradation of sulfur linkages and thiophenic rings caused by the biochemical treatment process of the present invention. The biotreatment results shown in FIG. 2 for bituminous coal are somewhat different from those obtained for lignite coals. PY-GC-FPD analyses illustrated in FIG. 2 show that there was a substantial degradation of the thiophenic ring type compounds with minor changes in the sulfide forms.

The graphs set forth in FIG. 2 show some noise or spurious signals known as artifacts. Pyrolysis of macromolecular substances such as coals and heavy crude oils are known to be subject to artifact formation. Recent studies of pyrolysis of fossil polymers at low temperature, i.e., 610° C. have indicated that products are formed mainly by cleavage of one bond at a time. Possible mechanisms of biochemical degradation of organic sulfur compounds by thermophiles may also involve a stepwise enzymatic breakdown of organic sulfur structures as found in kerogens. One example of such biochemical degradation is the flash pyrolysis product of alkylthiophenes as derivatives of their corresponding alkylthiophene moieties in kerogen. The results shown in FIG. 2 support the possible mechanisms of biodegradation discussed above.

The results set forth in FIG. 3 are discussed by reference to biodegradation of model organosulfur compounds ("OSC"). The biodegradation of OS compounds has been extensively reviewed by Fedorak, F. M. in "Geochemistry of Sulfur in Fossil Fuels, ACS Symposium Series 429, American Chemical Society, Washington, D.C., 93–112, 1990. In general, the biochemical reactions of model OS compound leads to the biodegradation of thiophenic compounds yielding hydroxy substituted rings, as well as open ring sulfones or sulfoxides. If similar biochemical reactions occur during the biotreatment of coals, the reduced sulfur forms may lead to a biochemical partial breakdown of coal structure observable in coal pyrolysis. Analysis of biotreated and untreated bituminous and lignite coal by PY-GC-MS as illustrated in FIG. 3, shows that the biotreated coal contained more small to medium molecular weight fractions versus high molecular weight residues. The effect is more pronounced in the biotreated lignite. It appears that the overall breakage of sulfide linkages leads to an extensive breakdown of crosslinking in lignite coal structure. As a result, such biochemical reactions may be useful in the pre-treatment of coal prior to mild gasification of coal as well as biodesulfurization of coal.

Example 4
X-Ray Absorption Fine Structure Spectroscopy Analysis

X-ray absorption spectroscopy measurements were performed at the National Synchrotron Light Source ("NSLS") X-19A beam line at BNL. The x-ray beam emitted from the storage ring was collimated by an adjustable vertical slit and was diffracted by a double crystal monochromator [Si(111)], which passed a narrow energy band. The overall energy resolution was estimated to be 0.5 eV at 2500 eV photon energy. Harmonic rejection was accomplished by slightly misaligning the crystal orientation so that the intensity of the monochromator Bragg peak was reduced by about 80%. A Stern-Heald type fluorescence detector as described in *Scientific Instrumentation*, 50, 1579 (1979) placed at 90° to the beam was used to measure the fluorescent x-ray which was emitted in the relaxation of the core hold. For accurate measurements of edge shift, the spectrometer was calibrated so that the white line maximum peak of the elemental sulfur correspond to 2472.1 eV. Spectra were recorded in four energy regions about the edges: 2.32 keV to 2.46 keV in 2 eV steps; 2461 eV to 2500 eV in 0.08 eV steps; 2501 eV to 2520 eV in 0.2 eV steps; and 2521 eV to 2800 eV in 3 eV steps. The samples of powdered coal (100 mesh) were held in the cell of a 6 μm thick polypropylene bag.

Due to the self-absorption effect the attenuated fluorescence spectra required correction. The method developed by Waldo and Penner-Hahn as described in Waldo, G. S. et al., *Geochimica et Cosmochimica Acts*, 55, 801–814 (1991) was adopted. Following this procedure, the data was normalized in the post-edge region to fit a tabulated x-ray absorption cross section known as McMaster table as more particularly described in McMaster, W. H. et al. UCRL - 50174, Sec II, Rev. 1, Natl. Techn. Inf. Serv., Springfield, Va. (1969). The normalized spectra were fitted with linear combinations of absorption spectra of a model compounds of sulfur, sulfide, disulfide, thiophene, sulfone, and sulfate using a non-linear least-squared procedure. The fitting range (2465–2485 eV) was selected so that the region contained the white-line maxima for all of the model compounds. The adjustable parameters for each model spectrum were a scaling factor and an optional energy offset. Typically, energy offset was less than 0.2 eV and not greater than 0.4 eV. The scaling factor directly reflected the quantitive amount of each sulfur form. XANES analyses of Kentucky bituminous samples are presented in FIG. 4. These analyses were used together with the results from Table 3 to calculate the percentage of each sulfur form as presented in Table 5 below. Each group of sulfur formed in the coal was calculated as mole percentage of total sulfur forms.

TABLE 5

XANES Analysis of Biotreated Kentucky No. 8 Bitmiinous Coal[d]

|  | Sulfides | Thiophenes | Sulfoxides | Sulfones | Sulfates |
|---|---|---|---|---|---|
| BNL-NZ Control[b] | 0.240 | 0.441 | 0.121 | 0.045 | 0.153 |
| BNL-NZ-3 Treated | 0.234 | 0.408 | 0.086 | 0.047 | 0.194 |
| BNL-NZ-5 Treated | 0.208 | 0.296 | 0.089 | 0.053 | 0.179 |
| BNL-TH-29[a] Control[c] | 0.184 | 0.303 | 0.109 | 0.055 | 0.239 |
| BNL-TH-29 | 0.198 | 0.198 | 0.177 | 0.045 | 0.173 |

Figure 4:
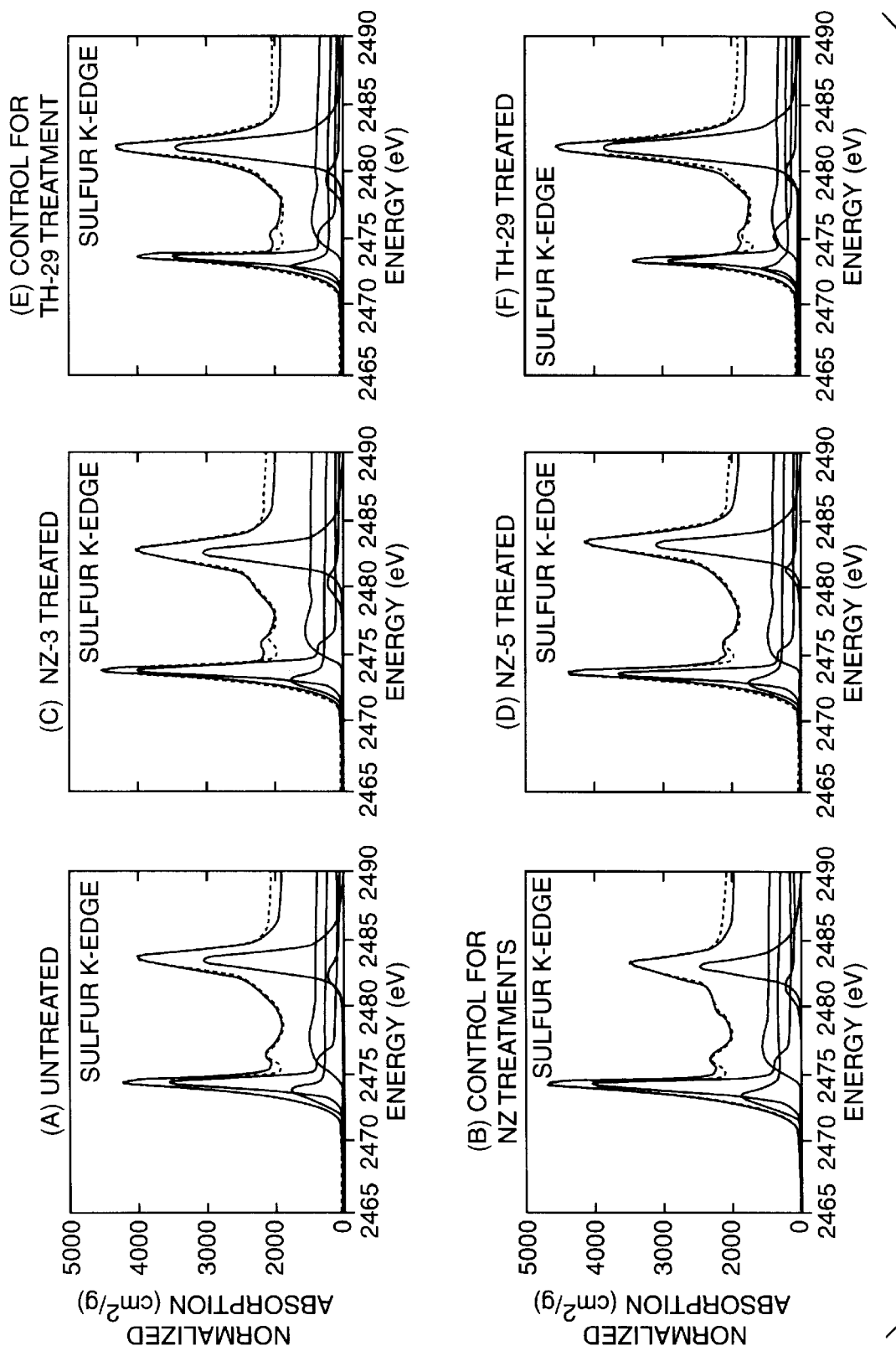
FIG. 4 shows x-ray absorption near edge structure spectroscopy (XANES) of Kentucky No. 8 bituminous coal, untreated and treated with modified strains of BNL-TH-29, BNL-NZ-3 and BNL-NZ-5 bacteria.

[a]Data have been normalized to 1.1% total sulfur content for untreated samples
[b]Control for NZ Medium
[c]Control for TH Medium
[d]Mole percentage of total sulfur form The XANES analysis of Kentucky No. 8 coal resolved the sulfur distribution in terms of a combination of representative groups of sulfur standards as illustrated in FIG. 4 and Table 5. A comparison of data for treated and untreated coal samples showed a significant decrease in thiophenic sulfur forms for bituminous coal treated with BNL-NZ-3, BNL-NZ-5 and BNL-TH-29 in a range from about 3.3 mol % to about 14.5 mol %.

The treatment of bituminous coal with both BNL-NZ-3 and BNL-NZ-5 resulted in a significant reduction of thiophenic sulfur and a smaller reduction of sulfoxide sulfur forms with small increases of sulfone and sulfate forms of sulfur. The increase in sulfones and sulfates is the result of bacterial oxidation of some of the sulfur compounds found in coal to sulfur oxide compounds. These results are similar to those obtained with aerobic oxidation of model compounds as discussed by Fedorak, F. M. in "Geochemistry of Sulfur in Fossil Fuels," ACS Symposium Series 429, American Chemical Society, Washington, D.C., 93–112, 1990. Additional reduction of thiophenic forms was found in the biotreatment with BNL-TH-29 strain with variable levels of reduction in sulfone, and sulfate forms and a slight increase in sulfoxides. After biotreatment, there was a small increase of sulfide forms. The results presented in Table 5 indicate that thiophenic forms of sulfur present in coal have been reduced and altered by biotreatment. These chemical changes in the organic sulfur forms present in coals can occur only if sulfur linkages are ruptured during biochemical treatment. These results are also consistent with those obtained by PY-GC-MS analysis as illustrated in FIG. 3.

Example 5

Trace Metal Analysis 50 mg samples of the desiccated coal obtained in Example 2 were digested according to the nitric vapor ashing method of Thomas A. D., et al., Talanta, 20, 469, 1973. The digested samples were dissolved in 1% $HNO_3$ and analyzed by vapor gas inductively coupled plasma mass spectrometer ("ICP-MS")model plasma Quad Plus 2. The results of the ICT-MS analysis are set forth in Table 6 below.

TABLE 6

Trace Metals Contents ($\mu$g/g)

| Trace Metals | Untreated Kentucky No. 8 | Biotreated Kentucky No. 8 |
|---|---|---|
| V | 157 | 99 |
| Mn | 168 | 41 |
| Cu | 143 | 0 |
| Sr | 1400 | 1040 |
| Y | 80 | 57 |
| Zr | 148 | 88 |
| La | 83 | 53 |
| Ce | 148 | 140 |
| Pb | 76 | 1 |
| Th | 34 | 23 |
| U | 19 | 0 |

The results set forth in Table 6 indicate that during biochemical transformation of coals the depolymerization and desulfurization of coal is accompanied by a significant overall decrease in trace metals present in coal.

The above experimental results obtained by two independent analytical methods, namely, PY-GC-MS and XANES, indicate that the biochemical treatment of coals according to the present invention provides a coal that has been desulfurized, depolymerized and demineralized.

Thus, while there have been described what are presently believed to be the preferred embodiments of the present invention, those skilled in the art will appreciate that other and further modifications can be made without departing from the true scope of the invention, and it is intended to include all such modifications and changes as come within the scope of the claims as appended herein.

We claim:

1. A process for biochemical upgrading of coal which comprises contacting a slurry of lignite or bituninous coal with a bacterial strain selected from the group consisting of Achromobactr sp. BNL-4-23 (ATCC 55021), Sulfolobus solfataricus BNL-TH-29 (ATCC 55022), Sulfolobus solfataricus BNL-TH-31 (ATCC 55023), Sulfolobus acidocaldarius BNL-TH-1 (ATCC 35091), Pseudomonas sp. BNL-4-24 (ATCC 55024), Leptospirillum ferrooxidans BNL-5-30 (ATCC 53992), Leptospirillum ferrooxidans BNL-5 -31 (ATCC 53993), Acinetobacter calcoaceticus BNL4-21 (ATCC 53996), Arthrobacter sp. BNL-4-22 (ATCC 53997), Acinetobacter calcoaceticus BNL-4-21s (ATCC 55489), Arthrobacters sp. BNL-4-22s (ATCC 55490), Achromobacter sp. BNL-4-23s (ATCC 55491), Pseudomonas sp. BNL4-24s (ATCC 55492), Mixed Culture R.I.-1 (ATCC 55501), Leptospirillum ferrooxidans BNL-5-30s (ATCC 55523), Leptospirillum ferrooxidans BNL-5-31s (ATCC 55524), Thiobacillus ferroxidans BNL-2-44s (ATCC 55525), Thiobacillus ferrooxidans BNL-2-45s (ATCC 55526), Thiobacillus ferrooxidans BNL-2-46s (ATCC 55527), Thiobacillus ferrooxidans BNL-2-47s (ATCC 55528), Thiobacillus ferrooxidans BNL-2-48s (ATCC 55529), Thiobacillus ferrooxidans BNL-2-49s (ATCC 55530), Unknown BNL-NZ-3 (ATCC 55488), Mixed Culture R.I.-2 (ATCC 55502), Mixed Culture R.I.-3 (ATCC 55503), Mixed Culture R.I.-4 (ATCC 55504), Mixed Culture R.I-5 (ATCC 55505), Mixed Culture R.I.-6 (ATCC 55506), Mixed Culture R.I.-7 (ATCC 55507), Mixed Culture R.I.-8 (ATCC 55508), Mixed Culture R.I.-9 (ATCC 55509), Mixed Culture R.I.-10 (ATCC 55510), Mixed Culture R.I.-11 (ATCC 55511), Mixed Culture R.I.-12 (ATCC 55512), Mixed Culture R.I.-13 (ATCC 55513), Mixed Culture R.I-14 (ATCC 5554) and mixtures thereof; and recovering the upgraded coal products.

2. The method of claim 1, wherein said coal slurry is comminuted to a particle size of about 100 mesh.

3. The method of claim 1, further comprising contacting said coal slurry with said bacterial strain at a temperature greater than about 40° C.

4. The method of claim 1, further comprising contacting said coal slurry with said bacterial strain at a reaction pressure of from atmospheric to about 2500 p.s.i.

5. The method of claim 1, further comprising contacting said coal slurry with said bacterial strain at a pH range from about 2 to about 10.

6. The method of claim 5, wherein said contacting is conducted at a pH of 4.

7. The method of claim 1, further comprising contacting said coal slurry with said bacterial strain at a salinity range from about 1.5 weight % to about 35 weight %.

8. The method of claim 1, wherein said bacterial strain has been modified to grow in the presence of toxic metal concentration from about 0.01 weight % up to about 10 weight %.

9. The method of claim 1, wherein said bacterial strain is added to said coal slurry in a aqueous solution which comprises nutrients.

10. The process of claim 1, wherein said bacterial strain is modified to utilize coal as sole source of carbon at a condition selected from the group consisting of a temperature range from about 40° C. to about 85° C., pressure range from atmospheric to about 2500 psi, a pH range from about 2 to about 10, a salinity range from about 1.5 weight % to about 35 weight % and a toxic metal concentration from about 0.01 weight % to about 10 weight %.

11. The process of claim 1, wherein said slurry of lignite bituminous coal contains sulftir from about 0.53% by weight to about 1.11% by weight, and trace metals from about 19 ppm to about 1400 ppm, said upgraded coal products containing organic sulfur decreased in an amount from about 7% by weight to about 13% by weight for lignite, from about 2% by weight to about 15% by weight bituminous coal and contents of trace metals decreased from about 5.4% by weight to about 100% by weight.

12. A process for biochemical upgrading of coal which comprises contacting a slurry of lignite or bituminous coal with a bacterial strain selected from the group consisting of *Acinetobacter calcoaceticus* BNL-4-21s (ATCC 55489), *Arthrobacter sp.* BNL-4-22s (ATCC 55490), *Achromobacter sp.* BNL-4-23s (ATCC 55491), *Pseudomonas sp.* BNL-4-24s (ATCC 55492), Mixed Culture R.I.-1 (ATCC 55501), *Leptospirillum ferrooxidans* BNL-5-30s (ATCC 55523), *Leptospirillum ferrooxidans* BNL-5-31s (ATCC 55524), *Thiobacillus ferrooxidans* BNL-2-44s (ATCC 55525), *Thiobaacillus ferrooxidans* BNL-2-45s (ATCC 55526), *Thiobacillus ferrooxidans* BNL-2-46s (ATCC 55527), *Thiobacillus ferrooxidans* BNL-2-47s (ATCC 55528), *Thiabacillus ferrooxidans* BNL-2-48s (ATCC 55529), *Thiobacillus ferrooxidans* BNL-2-49s (ATCC 55530), Unknown BNL-NZ-3 (ATCC 55488), Mixed Culture R.I.-2 (ATCC 55502), Mixed Culure R.I.-3 (ATCC 55503), Mixed Culture R.I.-4 (ATCC 55504), Mixed Culture R.I.-5 (ATCC 55505), Mixed Culture R.I.-6 (ATCC 55506), Mixed Culture R.I.-7 (ATCC 55507), Mixed Culture R.I.-8 (ATCC 55508), Mixed Culture R.I.-9 (ATCC 55509), Mixed Culture R.I.-10 (ATCC 55510), Mixed Culture R.I.-11 (ATCC 55511), Mixed Culture R.I.-12 (ATCC 55512), Mixed Culture R.I.-13 (ATCC 55513), Mixed Culture R.I.-14 (ATCC 5554) and mixtures thereof, and recovering the upgraded coal products.

13. A biochemical process for upgrading of a slurry of lignite or bituminous coal, which comprises:

(i) providing a thermophilic bacterial strain which is capable of growing on oil;

(ii) subjecting said thermophilic bacterial strain to sequential conditions comprising decreasing crude oil concentration and increasing coal concentration until coal is essentially the sole carbon source and increasing salinity and trace metal concentration stepwise until said thermophilic bacterial strain is capable of growing in coal as essentially the sole carbon source at a salinity level between 1.5 weight % to 35 weight % and a trace metal concentration from about 0.01 weight % to about 10 weight %;

(iii) contacting said modified thermophilic bacterial strain with said slurry wherein said bacterial strain is selected from the group consisting of *Acinetobacter Calcoalceticus* BNL-4-21s (ATCC 55489) *Arthrobacter sp.* BNL-4-22s (ATCC 55490), *Achromobacter sp.* BNL-4-23s (ATCC 55491), *Pseudomonas sp.* BNL-4-24s (ATCC 55492), Mixed Culture R.I.-1 (ATCC 55501), *Leptospirillum ferrooxidans* BNL-5-30s (ATCC 55523), *Leptospirillum ferrooxidans* BNL-5-31s (ATCC 55524), *Thiobacillus ferrooxidans* BNL-2-44s (ATCC 55525), *Thiobacmus ferrooxidans* BNL-2-45s (ATCC 55526), *Thiobacillus ferrooxidans* BNL-2-46s (ATCC 55527), *Thiobacillus ferrooxidans* BNL-2-47s (ATCC 55528), *Thiobacillus ferrooxidans* BNL-2-48s (ATCC 55529), *Thiobacillus ferrooxidans* BNL-2-49s (ATCC 55530), Unknown BNL-NZ-3 (ATCC 55488), Mixed Culture R.I.-2 (ATCC 55502), Mixed Culture R.I.-3 (ATCC 55503), Mixed Culture R.I.-4 (ATCC 55504), Mixed Culture R.I.-5 (ATCC 55505), Mixed Culture R.I.-6 (ATCC 55506), Mixed Culture R.I.-7 (ATCC 55507), Mixed Culture R.I.-8 (ATCC 55508), Mixed Culture R.I.-9 (ATCC 55509), Mixed Culture R.I.-10 (ATCC 55510), Mixed Culture R.I.-11 (ATCC 5551 1), Mixed Culture R.I-12 (ATCC 55512), Mixed Culture R.I-13 (ATCC 55513), and Mixed Culture R.I.-14 (ATCC 5554) and recovering the upgraded coal products.

* * * * *